United States Patent [19]

Khaled et al.

[11] Patent Number: 4,820,706

[45] Date of Patent: Apr. 11, 1989

[54] PTERIDINE DERIVATIVES AND METHOD OF TREATING LEUKEMIA EMPLOYING SAME

[75] Inventors: M. Abu Khaled, Helena; Frederick Benington; Richard D. Morin, both of Birmingham, all of Ala.

[73] Assignee: Research Corporation, New York, N.Y.

[21] Appl. No.: 822,988

[22] Filed: Jan. 27, 1986

Related U.S. Application Data

[63] Continuation-in-part of Ser. No. 576,581, Feb. 3, 1984, abandoned.

[30] Foreign Application Priority Data

Feb. 1, 1985 [CA] Canada ................................ 473410

[51] Int. Cl.⁴ ................. A61K 31/505; C07D 475/04; C07D 475/08
[52] U.S. Cl. .................... 514/249; 514/258; 544/258; 544/260; 544/261
[58] Field of Search ....................... 544/258, 260, 261; 514/249, 258

[56] References Cited

U.S. PATENT DOCUMENTS

2,563,707  8/1951  Cosulich ........................... 544/258
2,766,240 10/1956  Geraci ............................. 544/261

OTHER PUBLICATIONS

Cutting; W. C., *Cutting's Handbook of Pharmacology*, 4th ed. (1969: Appleton–Century–Crofts; New York), pp. 140–141.
Burger, A., *Medicinal Chemistry*, 2nd Ed., Interscience Publishers, Inc., New York, N.Y. (1960) pp. 1080–1085.
Henkin, J. et al., J. Med. Chem., 1983, 26, pp. 1193–1196.
Piper, J. R. et al., J. Med. Chem., 1985, 28, pp. 1016–1025.
Bunton, C. A. et al., J. Am. Chem. Soc., 1974, 96, pp. 3267–3275.

Primary Examiner—Donald G. Daus
Assistant Examiner—Mark W. Noel
Attorney, Agent, or Firm—Scully, Scott, Murphy & Presser

[57] ABSTRACT

2,4-Diaminopteridine derivatives and the pharmaceutically acceptable salts thereof having potent anticancer activity are disclosed. The derivatives possess the structural formula:

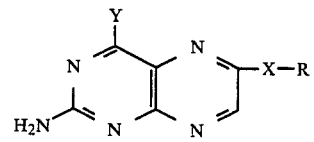

wherein Y is $NH_2$, OH or SH, R is

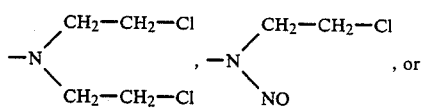

, or

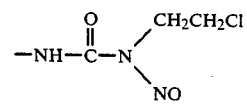

and X is

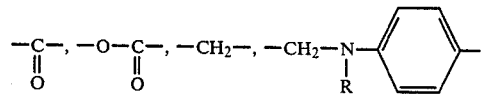

in which R' is H or $CH_3$ or

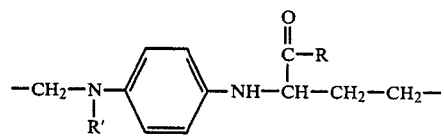

in which R and R' are as previously defined, provided when Y is $NH_2$, R' must be $CH_3$ and when Y is OH, R' must be OH.

6 Claims, 1 Drawing Sheet

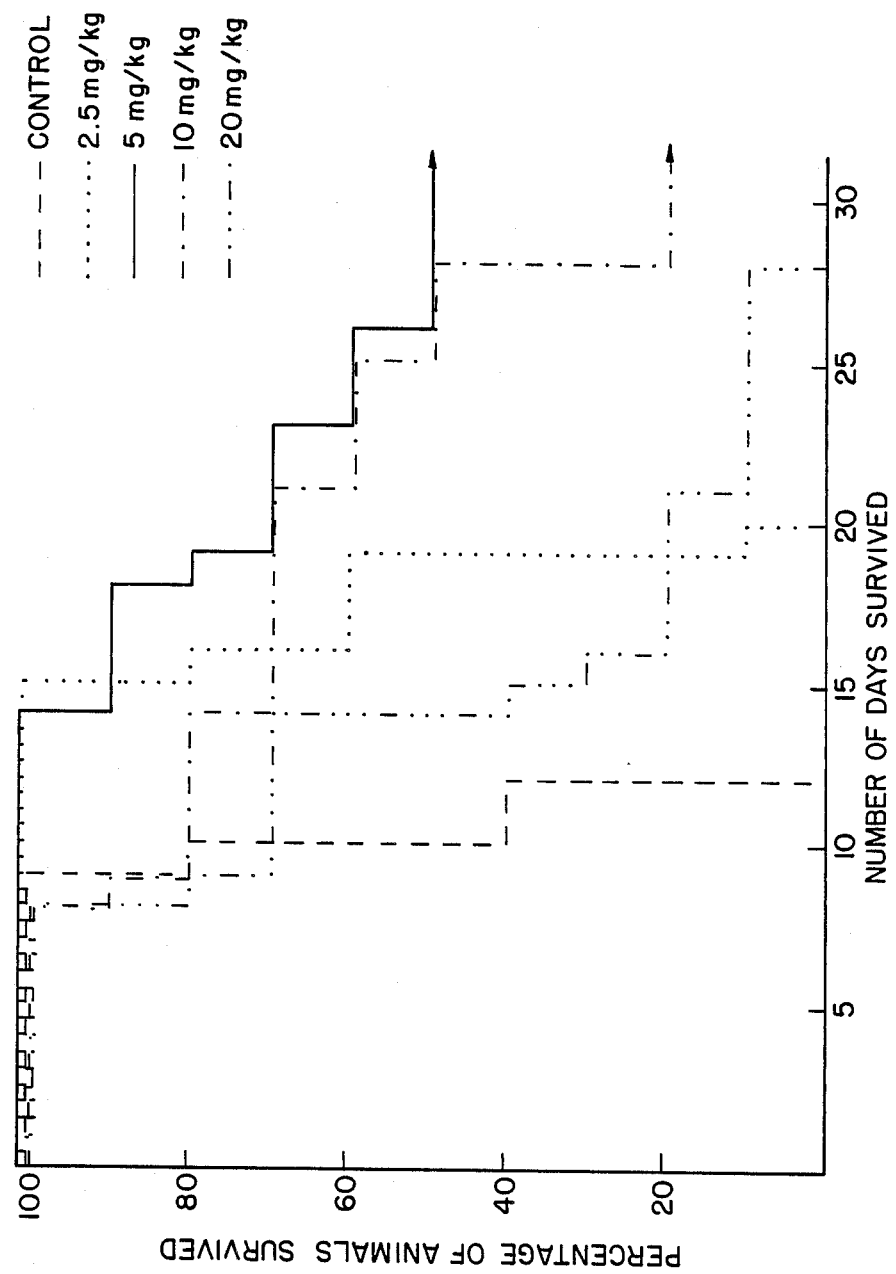

PTERIDINE DERIVATIVES AND METHOD OF TREATING LEUKEMIA EMPLOYING SAME

CROSS-REFERENCE TO RELATED APPLICATION

This application is a continuation-in-part of our co-pending application Ser. No. 576,581, filed Feb. 3, 1984 now abandoned.

BACKGROUND OF THE INVENTION

This invention relates to the pteridines generally, and more particularly, to pteridine derivatives bearing the particular alkylating moiety in the 6-position on the pteridine nucleus as hereinafter more fully disclosed. The invention also relates to pharmaceutical preparations containing the aforesaid pteridine derivatives as well as methods for treating cancers employing pteridines.

U.S. Pat. Nos. 4,077,957 and 4,374,987 describe procedures for preparing pteridine compounds including the anticancer drug methotrexate which possesses the structure

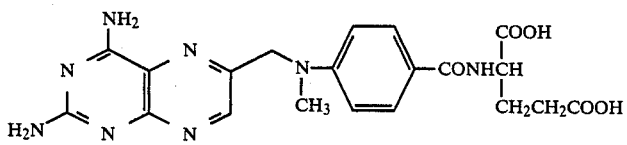

N-P-([2,4-diamino-6-pteridinyl)-methyl]methylamino)benzoyl glutamic acid and analogous compounds such as aminopterine

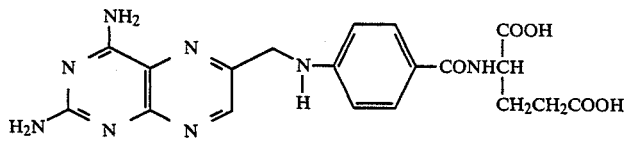

Methotrexate has in recent years become a prominent drug in the treatment of a variety of cancers (C. B. Pratt, et al., *Cancer Chemother. Rep.*, Part 3, 6, 13 (1975), the disclosure of which is incorporated by reference herein, and references cited).

BRIEF DESCRIPTION OF THE DRAWING

FIG. 1 is a graphic representation of the activity of the compound 2,4-diamino-6(bis-2-chloroethyl-)aminomethylpteridine evaluated in B6D2F1/J female mice (toxicity evaluation study-concentration dosage against time of survival).

SUMMARY OF THE INVENTION

In accordance with the present invention, pteridine derivatives and their pharmaceutically acceptable salts having potent anticancer activity and which are significantly more target specific than methotrexate and its analogs are provided. The pteridine derivatives of this invention possess the structural formula

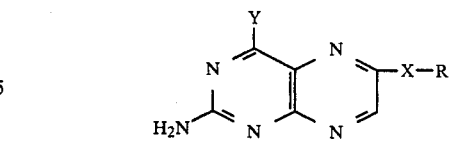

wherein Y is $NH_2$, OH or SH, R is

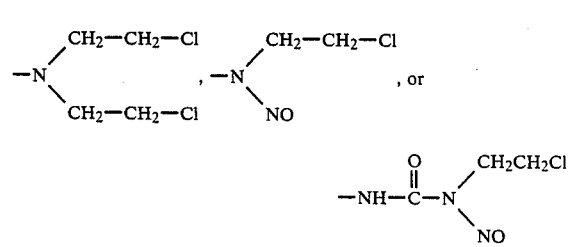

and X is

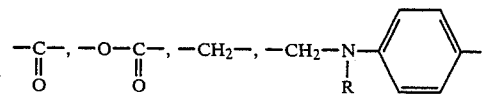

in which R' is H or $CH_3$ or

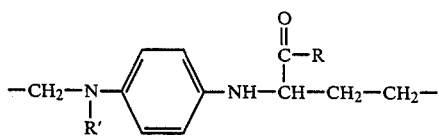

in which R and R' are as previously defined, provided, when Y is $NH_2$, R' must be $CH_3$ and when Y is OH, R' must be H.

DESCRIPTION OF THE PREFERRED EMBODIMENTS

The pteridine derivatives of the present invention can be readily prepared by those of ordinary skill in the art employing known and conventional syntheses. Thus, for example, preparation of the 2,4-diaminopteridine derivatives in which X is

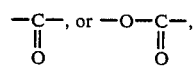

i.e., compounds of the formula

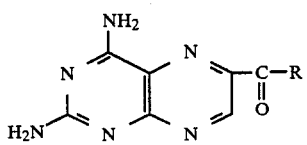 (I)

OR

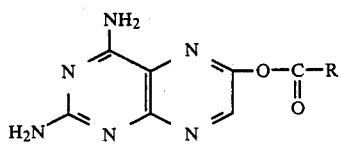 (Ia)

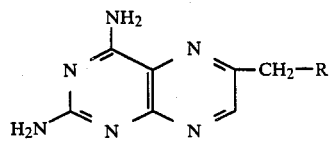 (II)

can also be readily prepared via known chemical syntheses.

For example, a 6-halomethyl derivative of 2,4-diamino-6(hydroxymethyl)-pteridine may be reacted with an appropriate amine, e.g., bis(2-chloroethyl)amine, to provide the desired derivative. An exemplary sequence of reactions is illustrated as follows:

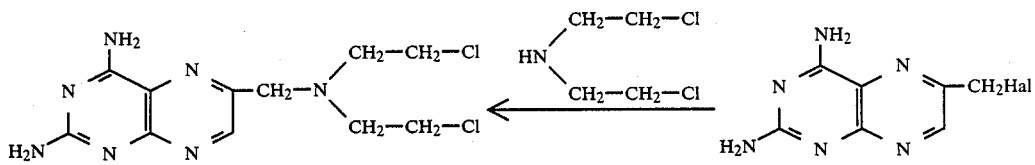

2,4-diamino-6-(bis-2-chloroethyl)aminomethylpteridine

The 6-halomethyl derivative may be prepared by halogenation of hydrohalide salt of the aforesaid known intermediate in the presence of a catalyst and in an aprotic solvent. The reaction sequence would be as follows:

can be obtained by reacting the corresponding carboxy acid, under amide-forming conditions, with an appropriate amine, to provide the desired derivative. An example of the sequence of reactions is illustrated as follows:

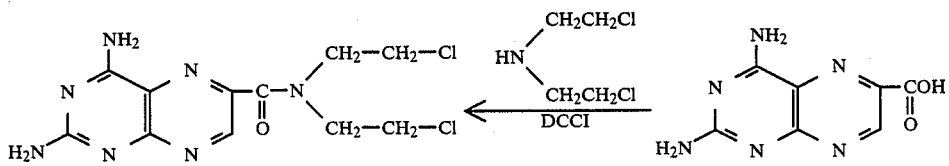

2,4-diamino-6-[(bis-2-chloroethyl)carboxamido]pteridine

The starting compound of the above scheme may be prepared by oxidation of 2,4-diamino-6-(hydroxymethyl)-pteridine, a known intermediate whose preparation is described in U.S. Pat. No. 4,077,957.

The amide forming conditions referred to herein involve the use of known derivatives of the described acids, such as the acyl halides, anhydrides, mixed anhydrides, lower alkyl esters, carbodiimides, carbonyl diimidazoles, and the like. The reactions are carried out in organic solvents such as acetonitrile, tetrahydrofuran, dioxane, acetic acid, methylene chloride, ethylene chloride and similar such solvents. The amide forming reaction will occur at room temperature or a elevated temperature. The use of elevated temperature is for convenience in that it permits somewhat shortened reaction periods. Temperatures ranging from 0° C. up to the reflux temperature of the reaction system can be used. As a further convenience the amide forming reaction can be effected in the presence of a base such as tertiary organic amines, e.g., trimethylamine, pyridine, picolines and the like, particularly where hydrogen halide is formed by the amide-forming reaction, e.g., acyl halide and amino compound. Of course, in those reactions where hydrogen halide is produced, any of the commonly used hydrogen halide acceptors can also be used.

The 2,4-diaminopteridine derivatives in which X is —CH$_2$—, i.e., compounds of the formula

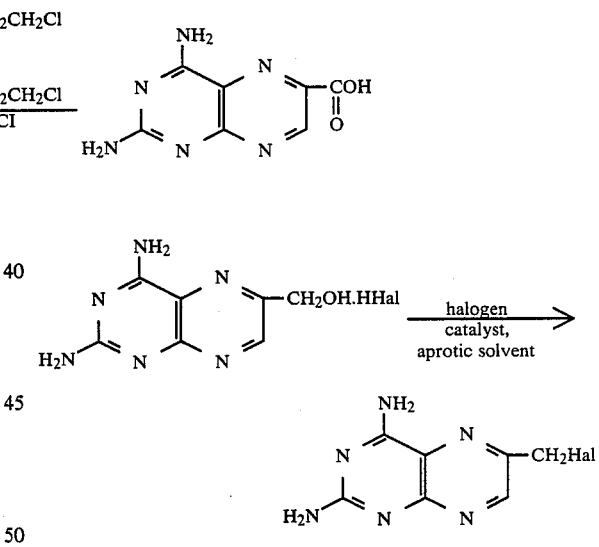

Appropriate catalysts in the above sequence would be, for example, triphenylphosphine and the like. Useful aprotic solvents include, among others, N,N-dimethylacetamide, N,N-diethylacetamide, 1-methyl-pyrrolidin-2 one, N,N-dimethylpropionamide, acetonitrile, benzonitrile tetrahydrofuran, dioxane and the like.

The 2,4-diaminopteridine derivatives in which X includes a phenylene group, i.e., compounds of the formulae

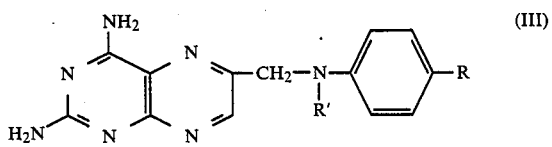 (III)

and

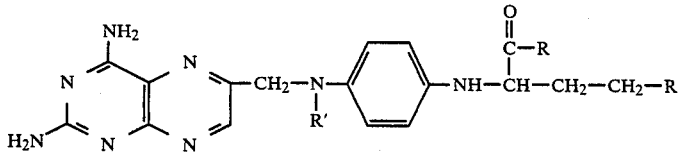

(IV)

can be prepared using syntheses which are analogous to the method for preparing derivatives (I) and (II) as described above.

The preferred amines in the reactions described with respect to both (I) and (II) have the formula

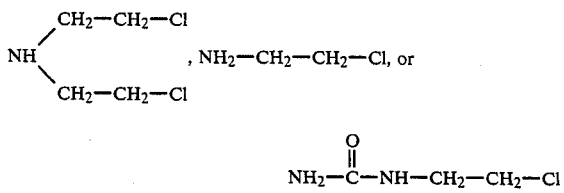

When the latter two amines are employed, nitrosation of the resulting product may optionally be performed by reaction with sodium nitrite in the presence of an acid.

The derivatives herein (which are inclusive of the pharmaceutically acceptable salts) can be formulated into a variety of dosage forms as is known in the art and utilized in the treatment of various cancers in the same manner as the currently used drug methotrexate.

Thus the active ingredients of the therapeutic compositions and the novel compounds of the present invention inhibit transplanted mouse tumor growth and induce regression and/or palliation of leukemia and related cancers in mammals when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 grams of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 milligrams of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearae; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compounds as free bases or pharmacologically acceptable salts can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged adsorption of the injectable compositions can be brought about by the use in the compositions of agents delaying absorption, for example, aluminum monostearate and gelatin.

Sterile injectable solutions are prepared by incorporating the active compounds in the required amounts in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 to 10 days are often sufficient. It is also possible to dispense one daily dosage or one dose on alternate or less frequency days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

Preparation of:

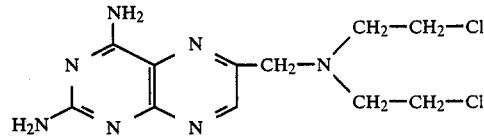

2,4-diamino-6-(bis-2-chloroethyl)aminomethylpteridine

A. 2,4-Diamino-6-(hydroxymethyl)-pteridine hydrochloride

To a solution of 42.8 g (0.167 mol) of 2,4,5,6-tetraminopyrimidine sulfate monohydrate, which had been recrystallized from boiling 1N sulfuric acid, in 700 ml of boiling water was added gradually a solution of 40.7 g (0.167 mol) of barium chloride dihydrate in 100 ml water. After a short period of digestion, the mixture was filtered from the precipitated barium sulfate, the filtrate was stirred with 5 g of decolorizing carbon and filtered again. This solution was added to a stirred mixture of 426 g of ammonium chloride, 26.3 g (0.167 mol) of cysteine hydrochloride, 46.6 g (0.259 mol) of dihydroxyacetone dimer and 970 mol of water in a 3-l three-necked flask equipped with a stirrer and a glass-fitted gas inlet tube. The resulting mixture was stirred for 67 hours at room temperature during which time a slow stream of oxygen was passed through the mixture via the gas inlet tube. The product, 2,4-diamino-6-(hydroxymethyl)-pteridine hydrochloride, separates as a tan solid which was collected by suction filtration, washed with water, and air dried; yield, 17.2 g (45%).

B. 2,4-Diamino-6-(bromomethyl)-pteridine hydrobromide

To a solution of 17.2 g of 2,4-diamino-6-(hydroxymethyl)-pteridine hydrochloride in 345 ml of hot water was added 50 ml of 28% aqueous ammonia. After cooling, the solid free base was filtered off and air dried; yield, 12.4 g (86%). A stirred mixture of this free base in 800 ml of boiling ethanol was treated with 7.5 ml of 48% hydrobromic acid and allowed to cool. The resulting hydrobromide salt was collected by suction filtration, washed with ethanol and air dried; yield 16.6 g (94%).

To a stirred solution of 63.9 g (0.244 mol) of triphenylphosphine in 325 ml of N,N-dimethylacetamide was added dropwise 39 g (0.244 mol) of bromine at a temperature of 10° to 12° C. To this stirred mixture was added 16.6 g of (0.061 mol) of 2,4-diamino-6-(hydroxymethyl)-pteridine hydrobromide in one portion. After stirring for 2 hours at 20°-25° C., 4 ml of ethanol was added, and the mixture was kept in a cold room (4° C.) overnight. Most of the N,N-dimethylacetamide was removed by distillation at a pressure of 1 mmHg and a pot temperature not exceeding 45° C. The residue was stirred with 190 ml of benzene, which was decanted from the insoluble semisolid residue. This procedure was repeated with another 190 ml portion of benzene, which was decanted from the insoluble semisolid residue. This procedure was repeated with another 190 ml portion of benzene, and the solid that remained was stirred at 80° C. with 435 ml of glacial acetic acid until solution was complete. This mixture was allowed to cool overnight, and the solid that separated was removed by filtration; yield 15.5 g. This crude product was recrystallized from boiling isopropanol, filtering from 5 g of insoluble material; yield of 2,4-diamino-6-(bromomethyl)-pteridine hydrobromide containing 0.5 mol of isopropanol of crystallization, 8.3 g (34.5).

C.
2,4-Diamino-6-bis(2-chloroethyl)aminomethylpteridine

To a solution of 4 g of 2,4-diamino-6-(bromomethyl)-pteridine hydrobromide in 150 ml of hot water was added 10 ml of 28% aqueous ammonia, and when cool the precipitated free base was filtered, washed with water, and air dried; yield, 2.94 g (94%).

To a stirred solution of 2.4 g (9.4 mmol) of 2,4-diamino-6-(bromomethyl)pteridine in 50 ml of N,N-dimethylacetamide was added 6 g (0.04 mol) of bis-(2-chloroethyl)amine, and the mixture was stirred at 50°-55° C. for 5 hours and then for 18 hours at room temperature. After filtering from a small amount of dark insoluble matter, the filtrate was diluted with 200 ml of water whereupon 2,4-diamino-6-bis(2-chloroethyl)-aminomethylpteridine separated as a light tan solid which was filtered, washed thoroughly with water and air dried; yield, 0.92 g (31%).

EXAMPLE 2

Preparation of:

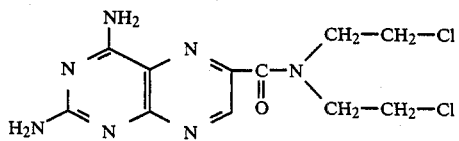

4 g of 2,4-diamino-6-(hydroxymethyl)-pteridine hydrochloride is dissolved in sodium bicarbonate and oxidized by $KNnO_4$. The oxidized product, 2,4-diamino-6(carboxy acid)pteridine, is obtained by neutralizing the reaction mixture with diluted $H_2SO_4$.

Synthetic Route 1: 2.5 g (9.5 mmol) of 2,4-diamino-6(carboxy acid)pteridine is dissolved in DMSO and added to 9.5 mmol of N,N'-dicyclohexylcarbodiimide (DCCI). To this reaction mixture is added 6 g (0.4 mmol) of bis(2-chloroethyl)amine and stirred for 18 hours at room temperature. The reaction mixture is then worked up in the same way as mentioned in step C, Example 1.

Synthetic Route 2: 2.5 g (9.5 mmol) of 2,4-diamino-6(carboxy acid)pteridine is dissolved in dry DMF. The solution is cooled to −5° C. To this solution was added 9.5 mmol of N-methylmorpholine and stirred for 15 minutes. To the stirred solution was added 9.5 mmol of ethylchloroformate and stirred for ½ hour. A freshly prepared bis(2-chloroethyl)amine (0.5 mmol) in DMF (chilled) was added dropwise. After ½ hour the reaction mixture is brought to room temperature and is left overnight. The reaction mixture is evaporated to dryness. The residue is dissolved in water and neutralized by adding diluted HCl or $NaHCO_3$ solution. The rest of the procedure is same as stated above.

EXAMPLE 3

Preparation of:

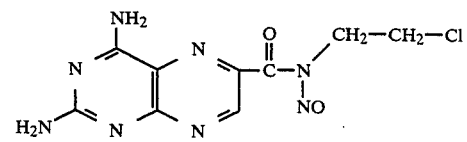

4 g of 2,4-diamino-6-(hydroxymethyl)pteridine hydrochloride is dissolved in sodium bicarbonate and oxidized by potassium permaganate. The oxidized product, 2,4-diamino-6-(carboxy acid)pteridine, is obtained by neutralizing the reaction mixture with dilute sulfuric acid. This oxidized product is dissolved in dimethylformamide and to which 9.5 mmol of DCCI was added. 6 mmol of 2-chloroethylamine monohydrochloride was added together with 6 mmol of N-methyl morpholine. The reaction mixture is stirred for 18 hours at room temperature and worked up in the same way as mentioned in step C of Example 1. Nitrosation of the reaction product with sodium nitrite/formic acid mixture provides the desired compound.

The following additional compounds within the scope of the present invention can be prepared employing analogous methods:

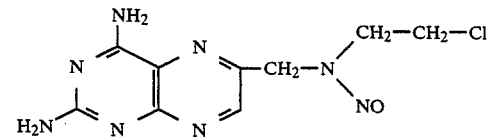

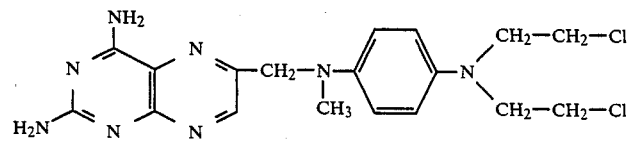

-continued
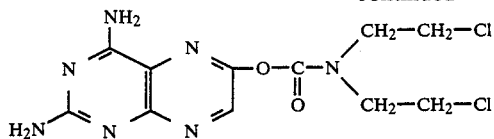
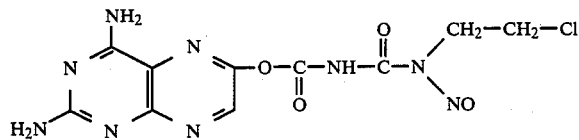
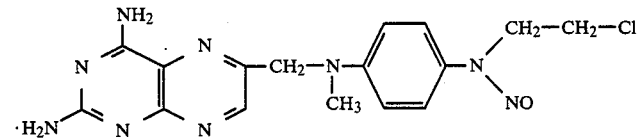
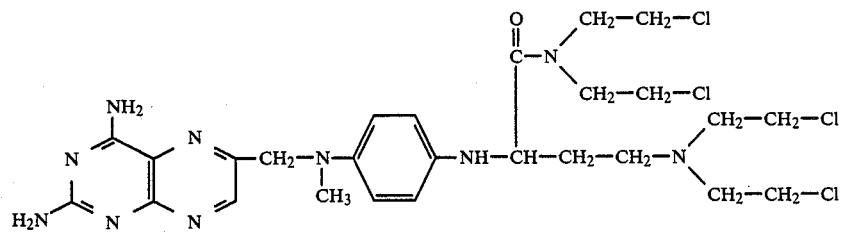
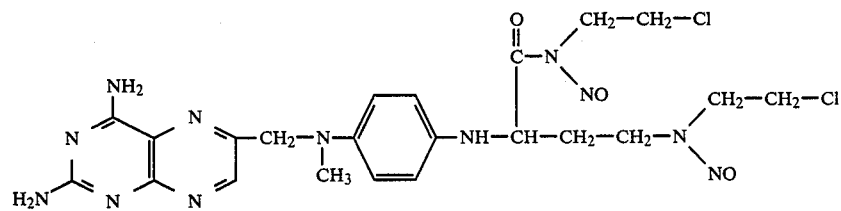
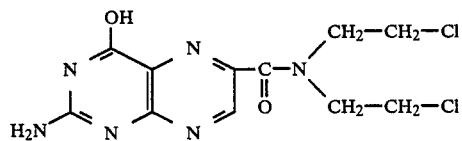
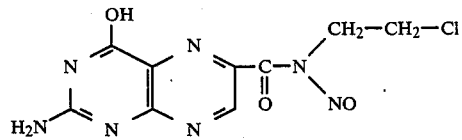
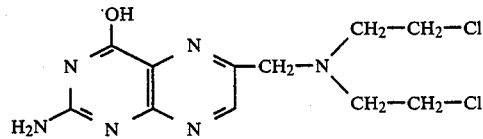
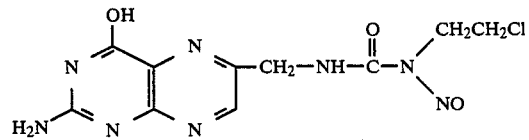
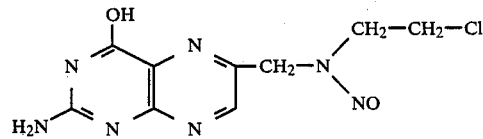

-continued
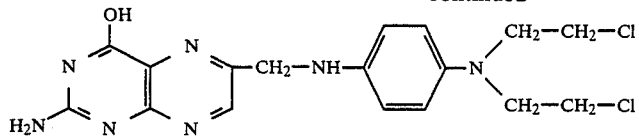
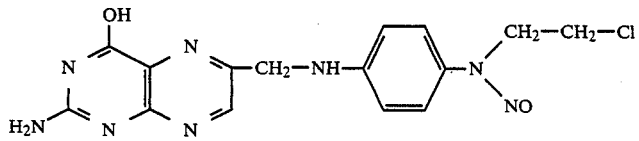
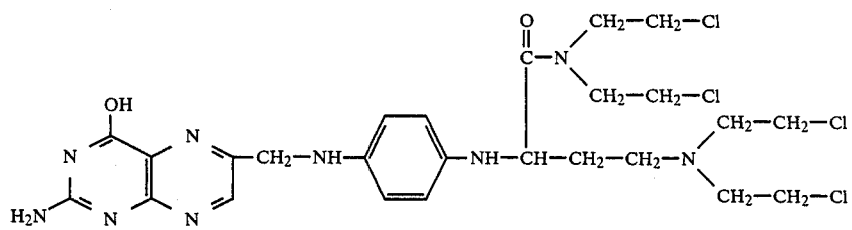
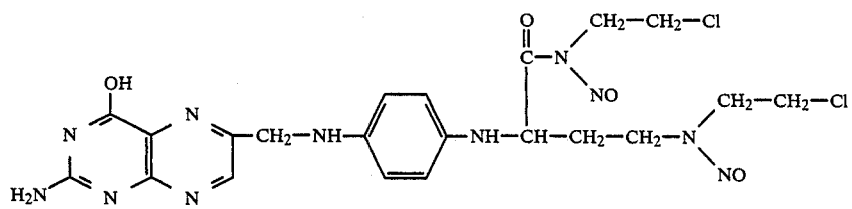
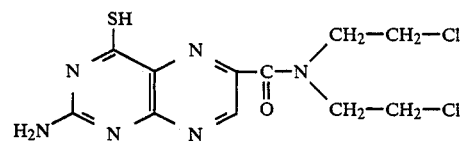
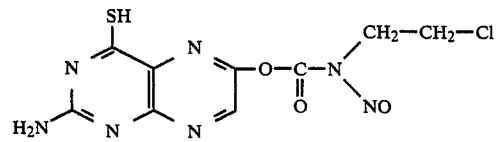
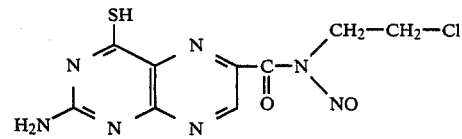
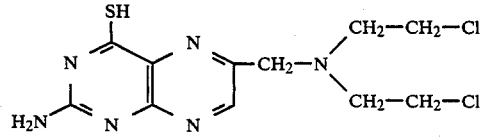
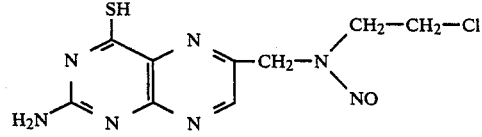
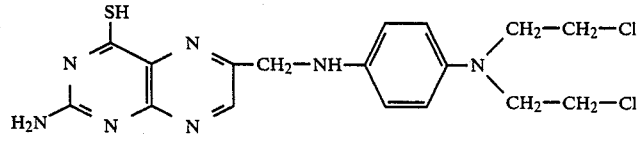

-continued

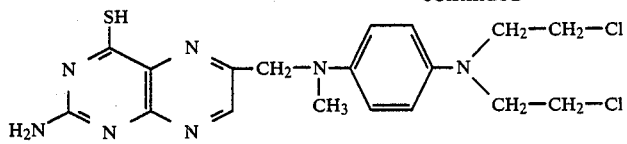

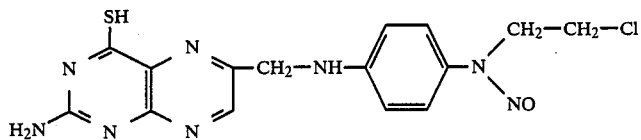

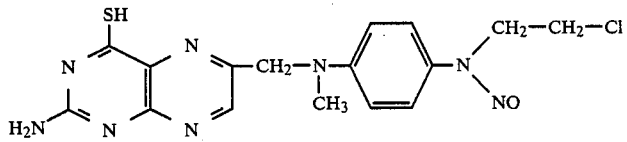

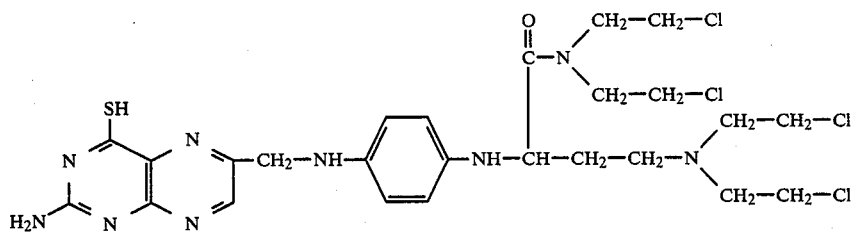

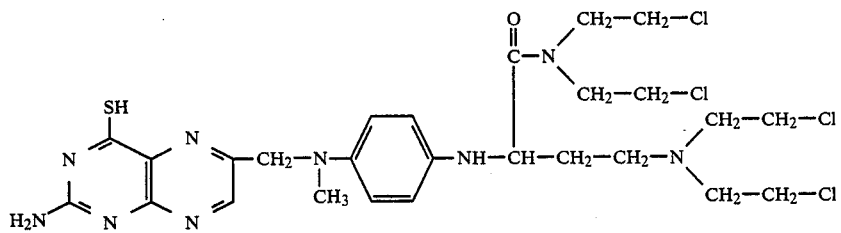

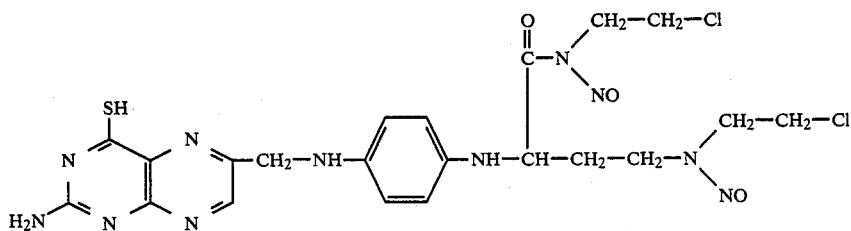

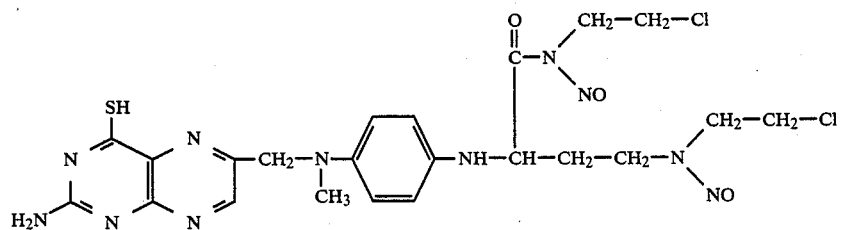

EXAMPLE 4

The potency of the compound of Example 1, i.e., 2,4-diamino-6(bis-2-chloroethyl)aminomethylpteridine, was evaluated in B6D2F1/J female mice, (Jackson Lab., Bar Harbor, ME.) During the course of the experiments, the animals were maintained in a controlled environment with limited accessibility and were permitted free access to food and water. They were divided in groups containing 10 animals in each group. The mice were inoculated intraperitoneally (I.P.) with $1 \times 10^5$ L-1210 mouse leukemia lymphoblasts. Day zero was the day when L-1210 was injected and the following day, Day 1, the treatment started. Initially the doses of the drug used were 2.5, 5, 10 and 20 mg/kg and they were used as suspension in distilled water. For the purpose of studying the apparent toxicity of this drug the above doses were also injected (I.P.) in normal mice of 9-11 weeks of age weighing 22-25 g per mouse. A volume of 0.2 to 0.3 ml of the suspension was injected in each animal. A single dose was used for both toxicity and activity studies.

The results from the toxicity studies showed no toxic death of animals from the dose that showed maximum activity, i.e., 5 mg/kg. The results of the drug activity are summarized in FIG. 1. As it can be seen, the drug had significant effect on the survivability of animals implanted with $1\times 10^5$ L-1210 tumor cells on Day 0. Several doses were examined and in each instance there was noticeable prolongation of lifespan compared to the control (broken line in FIG. 1). For example, animals receiving 2.5 mg/kg of the drug had an increased lifespan of 190%, while animals receiving 5 mg/kg dose showed a remarkable survivability (solid line in FIG. 1). This dose was repeated twice and in each study it showed the similar survival pattern, i.e., 50% of the animals had an increased lifespan of more than 200%, while the other 50% of the animals were totally cured and even remained alive at the end of 90 days. However, those animals receiving the drug at 10 and 20 mg/kg extended the lifespan 250 and 140%, respectively, and 20% of the animals treated with 10 mg/kg remained alive at the end of 30 days (see FIG. 1).

The activity of 2,4-diamino-6-(bis-2-chloroethyl)-aminoethylpteridine was also tested on solid tumor. BALB/C adult female mice were given $2\times 10^6$ viable MOPC 104E cells intravenously. 18 Days following the transplantation of tumor, when the tumor burden was large and at an advanced stage, the mice were treated with 5 mg/kg or this compound in suspension (I.P.). The increase in lifespan of mice was found to be 224% even when the treatment started at a very advanced stage of tumor growth (i.e., treatment started on the 18th day while the control died on the 20th day).

What is claimed is:

1. Compounds of the formula

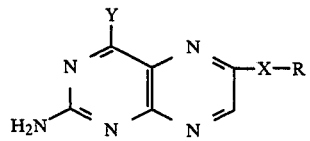

wherein Y is $NH_2$, OH or SH, R is

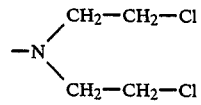

and X is

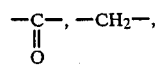

2. A compound of claim 1 of the formula

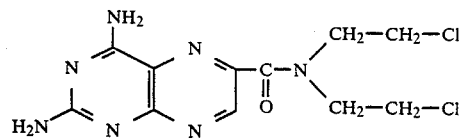

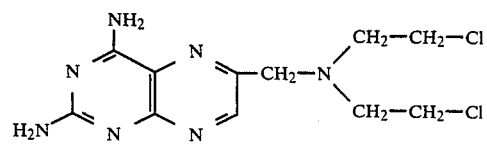

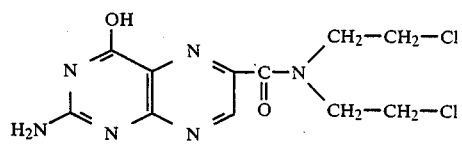

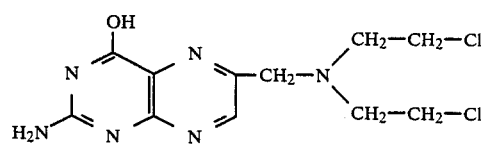

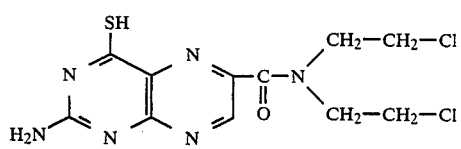

and the pharmaceutically acceptable salts thereof.

3. The method of inducing regression of leukemia in a mammal comprising administering to said mammal an effective antineoplastic amount of a compound of claim 1.

4. The method of inducing regression of leukemia in a mammal comprising administering to said mammal an effective antineoplastic amount of a compound of claim 2.

5. A pharmaceutical composition in dosage unit form for the regression of leukemia in a mammal comprising an effective amount of a compound of claim 1 sufficient to induce regression of leukemia, in association with a pharmaceutical carrier.

6. A pharmaceutical composition in dosage unit form for the regression of leukemia in a mammal comprising an effective amount of a compound of claim 2 sufficient to induce regression of leukemia, in association with a pharmaceutical carrier.

* * * * *

UNITED STATES PATENT AND TRADEMARK OFFICE
CERTIFICATE OF CORRECTION

PATENT NO. : 4,820,706
DATED : April 11, 1989
INVENTOR(S) : M. Abu Khaled, et al.

It is certified that error appears in the above-identified patent and that said Letters Patent is hereby corrected as shown below:

Column 7, line 66: "frequency" should read as --frequent--

Column 18, line 39, Claim 2: add the following formula:

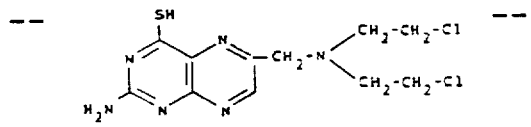

Signed and Sealed this

Twenty-seventh Day of March, 1990

Attest:

JEFFREY M. SAMUELS

*Attesting Officer*        *Acting Commissioner of Patents and Trademarks*